US012673019B2

(12) United States Patent
Gu

(10) Patent No.: US 12,673,019 B2
(45) Date of Patent: Jul. 7, 2026

(54) SKIN CARE COMPOSITION

(71) Applicant: Conopco, Inc., Englewood Cliffs, NJ (US)

(72) Inventor: Xuelan Gu, Shanghai (CN)

(73) Assignee: Conopco, Inc., Hoboken, NJ (US)

( * ) Notice: Subject to any disclaimer, the term of this patent is extended or adjusted under 35 U.S.C. 154(b) by 240 days.

(21) Appl. No.: 18/709,625

(22) PCT Filed: Nov. 7, 2022

(86) PCT No.: PCT/EP2022/080893
§ 371 (c)(1),
(2) Date: May 13, 2024

(87) PCT Pub. No.: WO2023/088698
PCT Pub. Date: May 25, 2023

(65) Prior Publication Data
US 2025/0000781 A1 Jan. 2, 2025

(30) Foreign Application Priority Data

Nov. 16, 2021 (WO) ................ PCT/CN2021/130878
Jan. 13, 2022 (EP) ..................................... 22151254

(51) Int. Cl.
| A61K 36/00 | (2006.01) |
| A61K 8/06 | (2006.01) |
| A61K 8/365 | (2006.01) |
| A61K 8/92 | (2006.01) |
| A61K 36/74 | (2006.01) |
| A61K 47/12 | (2006.01) |
| A61P 29/00 | (2006.01) |
| A61Q 19/08 | (2006.01) |

(52) U.S. Cl.
CPC .............. *A61K 8/922* (2013.01); *A61K 8/062* (2013.01); *A61K 8/365* (2013.01); *A61K 36/742* (2024.05); *A61K 47/12* (2013.01); *A61P 29/00* (2018.01); *A61Q 19/08* (2013.01)

(58) Field of Classification Search
CPC .................................................. A61K 36/742
See application file for complete search history.

(56) References Cited

U.S. PATENT DOCUMENTS

| 10,806,790 B1 | 10/2020 | Shapiro |
| 2008/0069784 A1 | 3/2008 | Millikin et al. |
| 2009/0143714 A1 | 6/2009 | Millikin et al. |
| 2014/0017341 A1 | 1/2014 | Gourlaouen |
| 2019/0151232 A1 | 5/2019 | Scharp |

FOREIGN PATENT DOCUMENTS

| CN | 108721158 A | * 11/2018 | ............. A61K 8/922 |
| CN | 112472622 | 3/2021 | |
| EP | 2561853 | 2/2013 | |

| WO | WO2009032699 | 3/2009 |
| WO | WO2014031958 | 2/2014 |
| WO | WO2014075157 | 5/2014 |

OTHER PUBLICATIONS

Tingyan Mi et al; Niacinamide and 12-hydroxystearic acid prevented benzo(a)pyrene and squalene Peroxides induced hyperpigmentation in skin equivalent; Experimental Dermatology; Dec. 5, 2018; pp. 4, XP055577077; John Wiley & Sons Ltd; Denmark.
Search Report and Written Opinion in PCTEP2022080893; Jan. 20, 2023; World Intellectual Property Org. (WIPO).
GNPD Database (Online) Mintel; Whipped Cream Coffee & Vanilaa Body Scrub; Nature's Kitchen; Jun. 2019; pp. 1-6, Record ID 6618991, XP055938033; United Kingdom.
Search Report and Written Opinion in EP22151254; Jul. 28, 2022; European Patent Office (EPO).
Kendall et al.; Distribution of Bioactive Lipid Mediators in Human Skin; Journal of Investigative Dermatology; Mar. 12, 2015; pp. 1510-1520; 135; The Society for Investigative Dermatology.
Regensburger et al.; Fatty acids and vitamins generate singlet oxygen under UVB irradiation; Experimental Dermatology; Nov. 8, 2011; p. 135-139; vol. 21(2) ; John Wiley & Sons A/S.
Cosgrove et al.; Dietary nutrient intakes and skin-aging appearance among middle-aged American women; American Journal of Clinical Nutrition; Oct. 2007; p. 1225-1231; vol. 86(4); American Society for Nutrition.
GNPD Database (Online) Mintel; Body Butter; The Cocoon Original Vietnam Dak Lak Coffee; May 2021; pp. 1-3, Record ID 8744019; Vietnam.
GNPD Database (Online) Mintel; Firming Sugar Scrub; Naturals by Watsons Coffee; Apr. 2021; pp. 1-3, Record ID 8629091; Hong Kong.
GNPD Database (Online) Mintel; Plump & Prime Luxury Face Plumping Primer Serum; Too Faced; Jan. 2021; pp. 1-5, Record ID 8404577; United Kingdom.
GNPD Database (Online) Mintel; Multi-Dimensional Repair Treatment Retinol; Clinique Clinique Smart Clinical MD; Jan. 2021; pp. 1-2, Record ID 8385487; United States of America.
GNPD Database (Online) Mintel; Multi-Dimensional Repair Treatment Retinol; Clinique Clinique Smart Clinical MD; Dec. 2020; pp. 1-4, Record ID 8385099; France.
GNPD Database (Online) Mintel; Multi-Dimensional Repair Treatment Retinol; Clinique Clinique Smart Clinical MD; Dec. 2020; pp. 1-4, Record ID 8385103; Germany.
GNPD Database (Online) Mintel; Facial Signature Set; Beigic; Dec. 2020; pp. 1-2, Record ID 8369621; Korea (South).
GNPD Database (Online) Mintel; Facial Duo; Beigic; Dec. 2020; pp. 1-2, Record ID 8369657; Korea (South).

(Continued)

*Primary Examiner* — Qiuwen Mi
(74) *Attorney, Agent, or Firm* — Stephanie Huang

(57) ABSTRACT

Disclosed is a skin care composition providing anti-inflammation benefits. The composition is comprising of coffee seed oil and a hydroxy-substituted $C_8$-$C_{24}$ fatty acid being 12-hydroxy stearic acid, wherein the weight ratio of the coffee seed oil to the hydroxy-substituted C8-C24 fatty acid is 1:5 to 15:1.

19 Claims, No Drawings

(56)        References Cited

OTHER PUBLICATIONS

GNPD Database (Online) Mintel; Under Eye Cream; The Moms Co. Natural Age Control; Nov. 2020; pp. 1-4, Record ID 8259789; India.

GNPD Database (Online) Mintel; Plump & Prime Luxury Face Plumping Primer Serum; Too Faced; Oct. 2020; pp. 1-5, Record ID 8179403; France.

GNPD Database (Online) Mintel; Smooth Move Body Cream; Mio Workout Wonders; Aug. 2020; pp. 1-5, Record ID 8048113; France.

GNPD Database (Online) Mintel; Smooth Move Body Cream; Mio Workout Wonders; Aug. 2020; pp. 1-4, Record ID 8048117; United Kingdom.

GNPD Database (Online) Mintel; Comforting Cream; Beigic; Feb. 2020; pp. 1-4, Record ID 7200701; Korea (South).

GNPD Database (Online) Mintel; Ultra-Hydrating Energy-Boosting Cream; Origins Ginzing; Feb. 2020; pp. 1-2, Record 7285821; Korea (South).

GNPD Database (Online) Mintel; Body Firming Gel; Nox by Natasha Coffee Gel Green Coffee; Oct. 2019; pp. 1-2, Record ID 6994399; Indonesia.

GNPD Database (Online) Mintel; Ultra-Hydrating Energy-Boosting Cream; Origins GinZing; Oct. 2019; pp. 1-2, Record ID 6952901; Belgium.

GNPD Database (Online) Mintel; Ultra-Hydrating Energy-Boosting Cream; Origins GinZing; Jul. 2019; pp. 1-2, Record ID 6763395; United States of America.

GNPD Database (Online) Mintel; Retinol Night Moisturizer with Alpine Flower; Origins Plantscription; May 2019; pp. 1-4, Record 6564941; France.

GNPD Database (Online) Mintel; Blue Serum; Chanel; Feb. 2019; pp. 1, Record ID 6317775; Japan.

GNPD Database (Online) Mintel; Coffee Body Scrub; Le Labo; Feb. 2018; pp. 1-2, Record ID 5446561; United States of America.

GNPD Database (Online) Mintel; Repair Night Cream; 100% Pure Organic High Potency Reversal; Oct. 2016; pp. 1-3, Record ID 4289549; United States of America.

GNPD Database (Online) Mintel; Aqua Shot Ampoule; The Oozoo; Sep. 2016; pp. 1-3, Record ID 4118687; Korea (South).

GNPD Database (Online) Mintel; Cool Fitting Body Gel; Missha; Jul. 2010; pp. 1-2, Record ID 1338395; Korea (South).

GNPD Database (Online) Mintel; Anti-Cellulite Range; Lancaster Sunslim Body Programme; Aug. 2007; pp. 1-2, Record ID 763704; United States of America.

GNPD Database (Online) Mintel; Celluli-Burner Tan Booster; Lancaster Sunslim Body Programme; Mar. 2006; pp. 1-2, Record ID 509656; France.

* cited by examiner

SKIN CARE COMPOSITION

CROSS REFERENCE TO RELATED APPLICATIONS

The present application is a U.S. National Phase Application under 35 U.S.C. § 371 of International Application No. PCT/EP2022/080893, filed on Nov. 7, 2022, which claims priority to International Application No. PCT/CN2021/130878, filed on Nov. 16, 2021, and European Patent Application No. 22151254.4, filed on Jan. 13, 2022, the contents of which are incorporated herein in their entireties.

FIELD OF THE INVENTION

The present invention relates to a skin care composition. In particular, the present invention relates to a skin care composition for providing enhanced anti-inflammatory efficacy.

BACKGROUND OF THE INVENTION

Inflammation is a complex biological host response to harmful stimuli such as pathogens, irritants or injury. Immune responses in the skin are important for host defence against pathogenic factors. However, dysregulated immune reactions can cause a few inflammatory skin symptoms.

Some consumers desire good-looking skin, but in real life they often encounter various skin problems caused by inflammation, for example, acne, post-inflammatory hyperpigmentation (PIH) and aging. Acne, also known as Acne vulgaris, is a common inflammatory skin problem which affects the pilosebaceous units of the skin. It can leave the subjects with severe skin scarring and also have severe psychological effects.

PIH is a hyperpigmentation of the skin occurring during or after an inflammatory process. PIH can be observed in any skin type and at all ages. In most case, PIH exerts a strong impact on the quality of life of affected individuals. External insults such as ultraviolet light exposure could also cause inflammation, which may enhance skin aging even further leading to signs of photoaging.

A few approaches have been taken to cope with inflammation-related problems, including topical and systemic treatments using antibiotics or steroids. However, those treatments may be irritating or may have other side effects. For example, antibiotics may cause antibiotic resistance. Therefore, there is still a need to develop new solutions for anti-inflammatory benefits.

Coffee is one of the most consumed beverages on earth. Coffee beans, the seeds of berries from certain *Coffea* species, are usually roasted to produce a cup of coffee. Coffee seed oil is the oil extracted from unroasted or roasted coffee seeds. Coffee seed oil may be extracted by the method of cold pressed distillation from the unroasted or roasted coffee seeds. Coffee seed oil is an ingredient sometimes used in skin care products.

Koffee'UP™, oil of roasted *Coffea arabica* seeds, is a product from Givaudan manufactured via drying spent coffee grounds followed by supercritical $CO_2$ extraction. According to Givaudan, its balance between saturated and unsaturated fatty acids helps the oil to quickly penetrate the skin layers.

In the market, cosmetic preparations containing coffee seed oil are known. For example, Clinique Smart Clinical MD collection is a skin care product described for anti-aging. Among the ingredients, coffee seed oil is said to be part of a comforting hydrator blend.

The present inventors have surprisingly found that a skin care composition comprising coffee seed oil and 12-hydroxy stearic acid provides enhanced anti-inflammatory benefit.

SUMMARY OF THE INVENTION

In a first aspect, the present invention provides a skin care composition comprising:
- (a) coffee seed oil; and
- (b) a hydroxy-substituted $C_8$-$C_{24}$ fatty acid, being 12-hydroxy stearic acid,
- wherein the weight ratio of the coffee seed oil to the hydroxy-substituted $C_8$-$C_{24}$ fatty acid is 1:5 to 15:1.

In a second aspect, the present invention provides a method for providing at least one benefit selected from anti-inflammation, anti-aging, and anti-acne comprising the step of applying the composition of the present invention to the skin of an individual.

In a third aspect, the present invention provides use of the composition of the present invention for providing at least one benefits selected from anti-inflammation, anti-aging, and anti-acne.

In a fourth aspect, the present invention provides the composition of the present invention for use in providing at least one benefits selected from anti-inflammation, anti-aging, and anti-acne.

In a fifth aspect, the present invention provides use of the composition of the present invention in the manufacture of a medicament in providing at least one benefits selected from anti-inflammation, anti-aging, and anti-acne.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Coffee Seed Oil

Coffee seed oil is the oil extracted from the beans of certain *Coffea* species. It can be extracted from unroasted coffee beans or roasted coffee beans. Coffee seed oil is rich in saturated fatty acids, unsaturated fatty acids and tocopherols. Due to these properties, coffee seed oil is sometimes used in skin care products. The composition of coffee seed oil varies according to the process of manufacture and

*Coffea* species. For example, unroasted coffee seed oil may contain higher level of fatty acids, vitamins and coffein.

Koffee'UP™, from Givaudan, is oil of roasted *Coffea arabica* seeds. It is manufactured from drying spent coffee grounds followed by supercritical $CO_2$ extraction. Koffee'UP™ is claimed to protect the skin and help the skin to stay hydrated.

The composition of the present invention comprises coffee seed oil. Preferably, the coffee seed oil is extracted from roasted seeds of coffee, more preferably from roasted seeds of coffee selected from *Coffea arabica, Coffea canephora* and *Coffea liberic*, and most preferably from roasted seeds of coffee from *Coffea arabica*.

Preferably, the coffee seed oil is employed in the composition in an amount of 0.00001 to 1% by weight of the composition, more preferably in an amount of 0.0001 to 0.5%, even more preferably from 0.0005 to 0.2% and most preferably in an amount of 0.001 to 0.05% by weight of the composition.

Hydroxy-Substituted $C_8$-$C_{24}$ Fatty Acid

The hydroxystearic acid of the present invention is 12-hydroxystearic acid (12HSA).

Preferably, the amount of hydroxy-substituted $C_8$-$C_{24}$ fatty acid is in the range of 0.000001 to 5%, more preferably 0.00001 to 1%, even more preferably 0.00005 to 0.2%, and still even more preferably 0.0001 to 0.01% by weight of the composition.

Preferably, the amount of 12-hydroxystearic acid (12HSA) is in the range of 0.000001 to 5%, more preferably 0.00001 to 1%, even more preferably 0.00005 to 0.2%, and still even more preferably 0.0001 to 0.01% by weight of the composition.

The weight ratio of the coffee seed oil to the hydroxy-substituted $C_8$-$C_{24}$ fatty acid is from 1:5 to 15:1, and preferably from 1:4 to 10:1.

Preferably, the weight ratio of the coffee seed oil to 12-hydroxystearic acid is from 1:5 to 15:1, and more preferably from 1:4 to 10:1.

Furthermore, it is within the scope of the present invention to include salt of 12-hydroxystearic acid, especially, sodium salt. However, it is preferred that 12-hydroxystearic acid is free 12-hydroxystearic acid.

Skin Benefit Agents

The composition of the invention may preferably further comprise a skin benefit agent selected from Vitamin B3 compounds, resorcinol compounds and mixtures thereof.

Vitamin B3 compounds (including derivatives of vitamin B3) e.g. niacin, nicotinic acid, picolinamide, isonicotinamide or niacinamide are the preferred skin benefit agents as per the invention, most preferred being niacinamide. Vitamin B3 compounds, when used, are preferably present in an amount in the range of 0.1 to 10%, more preferably 0.2 to 5% by weight of the composition.

Resorcinol compounds include resorcinol and its derivatives. Preferably, resorcinol derivative is 4-substituted resorcinol derivative selected from the group consisting of 4-linear alkyl resorcinols, 4-branched alkyl resorcinols, 4-cycloalkyl resorcinols and mixtures thereof. More preferably, the 4-substituted resorcinol derivative is 4-methyl resorcinol, 4-ethyl resorcinol, 4-propyl resorcinol, 4-butyl resorcinol, 4-pentyl resorcinol, 4-hexyl resorcinol, 4-heptyl resorcinol, 4-octyl resorcinol, 4-nonyl resorcinol, 4-decyl resorcinol, 4-cyclopentyl resorcinol, 4-cyclohexyl resorcinol, 4-cycloheptyl resorcinol, 4-cyclooctyl resorcinol or a mixture thereof. Most preferably the 4-substituted resorcinol derivative is 4-hexyl resorcinol.

Carrier

Compositions of the present invention may comprise a cosmetically acceptable carrier. Water is the most common carrier. Oily carriers in the presence of water and an emulsifier will form emulsion system as carriers. These systems may either be water-in-oil or oil-in-water emulsions, preferably oil-in-water emulsions. Besides water, suitable carrier classes include silicones, hydrocarbons, polyhydric alcohols, fatty alcohols, triglycerides or a mixture thereof.

Silicones when present may range from 5 to 60%, more preferably from 5 to 40%, by weight of the composition. These silicones may be organic, silicone-containing or fluorine-containing, volatile or non-volatile, polar or non-polar.

Particularly preferred volatile silicone oils are cyclic volatile silicones wherein the repeating unit ranges from 3 to 5; and linear silicones wherein the repeating unit ranges from 1 to 7. Highly preferred examples of volatile silicone oils include cyclomethicones of varying viscosities, e.g., Dow Corning 200, Dow Corning 244, Dow Corning 245, Dow Corning 344 and Dow Corning 345 (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.).

Hydrocarbons may include mineral oil, petrolatum and polyalpha-olefins. Examples of preferred volatile hydrocarbons include polydecanes such as isododecane and isodecane (e.g. Permethyl-99A which is available from Presperse Inc.) and the $C_7$-$C_8$ through $C_{12}$-$C_{15}$ isoparaffins (such as the Isopar Series available from Exxon Chemicals).

Polyhydric alcohols may include propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin. The amount of polyhydric alcohol may range anywhere from 0.1 to 10%, preferably between 0.4 and 5% by weight of the composition.

Fatty alcohols may also be present. The term "fatty alcohols" refers to alcohols having carbon chain with lengths ranging from 10 to 30 carbon atoms. Illustrative of this category are lauryl alcohol, cetyl alcohol, stearyl alcohol, isostearyl alcohol and combinations thereof. Cetyl alcohol is more preferable.

Illustrative triglycerides but not limiting are sunflower seed oil, cotton oil, canola oil, soybean oil, castor oil, borage oil, olive oil, shea butter, jojoba oil and mixtures thereof. Mono- and di-glycerides may also be useful. Particularly preferable are glyceryl monostearate and glyceryl distearate.

The composition may comprise water in amount of 10 to 90% by weight of the composition, preferably from 35 to 85%, more preferably between 40 and 70% by weight of the composition.

The composition may comprise optional ingredients including, preservatives, antioxidants, colorants, fragrance, or a combination thereof.

Suitable preservatives for the present invention include alkyl esters of para-hydroxybenzoic acid, isothiazolinones, DMDM hydantoin derivatives, propionate salts, and a variety of quaternary ammonium compounds, e.g. iodopropynyl butyl carbamate, phenoxyethanol, methyl paraben, propyl paraben, imidazolidinyl urea, sodium dehydroacetate and benzyl alcohol.

Suitable antioxidants for the present invention include Vitamin C, Vitamin E, CoQ10, polyphenols from various naturals e.g. tea and grapes.

US 12,673,019 B2

5

Viscosity

"Viscosity" as used herein means dynamic viscosity at 25° C. and is reported as mPa·s. A suitable method of measuring the viscosity is to use a stress-controlled MCR 501 rheometer (Anton Paar, Physica MCR501, Austria), fitted with a sandblast parallel geometry (PP25s), at shear rate 3.98 1/s.

The viscosity of the composition suitably ranges from 1,000 to 20,000 mPa·s, preferably from 2,000 to 15,000 mPa·s, even more preferably from 2,500 to 12,000 mPa·s.

Method and Use of the Skin Care Composition

A skin care composition as used herein includes a composition for topical application to the skin of mammals, especially humans. Such a composition could be of the leave-on or of the wash-off type. Wash-off type is sometimes also referred to as rinse-off type. A leave-on composition means a composition that is applied to the desired skin surface and left on for example from one minute to 24 hours, after which it may be wiped or rinsed off with water, usually during the regular course of personal washing. A wash-off composition means a composition that is applied to the desired skin surface for a shorter period, for example, a few seconds or minutes and usually contains sufficient surfactants that aids in cleaning the surface which may be rinsed off with copious amounts of water. The composition of the present invention is in the form of a liquid, lotion, cream, foam, scrub, or gel form.

The term "skin" as used herein includes the skin on the face (except eye lids and lips), neck, chest, abdomen, back, arms, under arms, hands, and legs. Preferably "skin" means includes the skin on the face (except eye lids and lips) and under arms, more preferably skin means skin on the face other than lips and eyelids.

The present invention also provides a skin care composition comprising coffee seed oil and a hydroxy-substituted $C_8$-$C_{24}$ fatty acid, for use in providing at least one benefits selected from anti-inflammation, anti-aging, and anti-acne.

The present invention also provides use of a combination of coffee seed oil and a hydroxy-substituted $C_8$-$C_{24}$ fatty acid, in the manufacture of a medicament for providing at least one benefit selected from anti-inflammation, anti-aging, and anti-acne.

The present invention also provides use of a composition comprising coffee seed oil and a hydroxy-substituted $C_8$-$C_{24}$ fatty acid for providing at least one benefits selected from anti-inflammation, anti-aging, and anti-acne.

Preferably, the method is non-therapeutic. Preferably, the use is non-therapeutic. The term non-therapeutic means for cosmetic purposes and not curative or therapeutic purposes.

For the present invention, "cosmetic" is intended to mean a non-pharmaceutical, non-therapeutic use, which is not intended for prevention and/or treatment of skin evaluated as pathological by a specialist in the field such as a dermatologist. For example, when the present invention is applied for skin anti-aging, it is a non-therapeutic use starting from non-pathological state.

The following examples are provided to facilitate an understanding of the invention. The examples are not intended to limit the scope of the claims.

EXAMPLES

Koffee'UP™ (Coffea arabica seed oil) used in the examples was obtained from Givaudan France SAS.

12HSA was purchased from Sigma-Aldrich (Cat No. 219967).

6

Human Immune Cell Line THP-1 In Vitro Assay

The following procedure was used to determine the anti-inflammation efficacy:

THP1-XBlue™ (Cat No. thpx-sp, InvivoGen, San Diego, CA) cells were cultured as suspension in RPMI 1640 medium supplemented with 10% fetal bovine serum (FBS), penicillin (10 U/mL)-streptomycin (10 μg/mL) (Cat No. 15140122, Invitrogen, Carlsbad, CA). Cells were differentiated in 24-well plates at the density of $5\times10^5$ cells/well with 100 nM phorbol-12-myristate-13-acetate for 72 hours. Cells were then co-treated with pure E. coli lipopolysaccharides (LPS, Cat No. L2630, Sigma-Aldrich) and various compositions in Table 1. After 24 hours, the supernatants were collected and measured for interleukin (IL)-6 as a pro-inflammatory biomarker using an enzyme-linked immunosorbent assay kit (Cat No. 555220, BD Biosciences, San Diego, CA). Expression of IL-6 was calculated as the percentage to LPS-treated cells which was designated as 100%. P value was analysed by Student's t-test comparing combination groups and individual compound groups (expression of IL-6, three repeats for each group). P value<0.05 indicates enhanced effect.

The results in terms of expression of IL-6 in percentage are given in Table 1:

TABLE 1

| Examples | Composition | Expression of IL-6 (%) | Std. dev | P value |
|---|---|---|---|---|
| A | LPS | 100 | 0 | — |
| B | 12HSA (6 ppm) | 84.4 | 5.4 | — |
| C | Koffee'UP ™ (100 ppm) | 45.0 | 2.7 | — |
| D | Koffee'UP ™ (100 ppm) + 12HSA (6 ppm) (Koffee'UP ™:12HSA = 17:1) | 34.7 | 4.2 | — |
| E | Koffee'UP ™ (10 ppm) | 78.7 | 7.1 | — |
| 1 | Koffee'UP ™ (10 ppm) + 12HSA (6 ppm) (Koffee'UP ™:12HSA = 1.7:1) | 56.0 | 8.6 | <0.05 |
| F | Koffee'UP ™ (1 ppm) | 100.6 | 4.3 | — |
| G | Koffee'UP ™ (1 ppm) + 12HSA (6 ppm) (Koffee'UP ™:12HSA = 0.17:1) | 71.6 | 6.1 | — |

From the above table it is evident that Example 1 within the scope of the present invention provides enhanced inhibition of IL-6 expression in THP-1 cells when compared with the examples that are outside the scope of the present invention (Example D and G).

The invention claimed is:

1. A skin care composition comprising:
(a) coffee seed oil; and
(b) a hydroxy-substituted $C_8$-$C_{24}$ fatty acid being 12-hydroxystearic acid,
wherein the weight ratio of the coffee seed oil to the hydroxy-substituted $C_8$-$C_{24}$ fatty acid is 1:5 to 15:1.

2. The skin care composition according to claim 1, wherein the composition comprises coffee seed oil extracted from roasted seeds of coffee selected from Coffea arabica, Coffea canephora and Coffea liberic.

3. The skin care composition according to claim 1, wherein the coffee seed oil is present in an amount of 0.00001 to 1% by weight of the composition.

4. The skin care composition according to claim 1, wherein the hydroxy-substituted $C_8$-$C_{24}$ fatty acid is present in an amount of 0.000001 to 5% by weight of the composition.

5. The skin care composition according to claim 1, wherein the weight ratio of the coffee seed oil to the 12-hydroxy stearic acid-is is 1:4 to 10:1.

6. The skin care composition according to claim 1, wherein the composition further comprises an additional skin benefit agent.

7. The skin care composition according to claim 6, wherein the skin benefit agent is selected from Vitamin B3 compounds, resorcinol compounds and mixtures thereof.

8. The skin care composition according to claim 1, wherein the composition comprises water in an amount of 10 to 90% by weight of the composition.

9. The skin care composition according to claim 1, wherein the viscosity of the composition is in the range of 1,000 to 20,000 mPa·s.

10. The skin care composition according to claim 1, wherein the composition is of the leave-on or of the wash-off type.

11. The skin care composition according to claim 1, wherein the composition is in the form of a liquid, lotion, cream, foam, scrub, or gel.

12. The skin care composition according to claim 1, wherein the composition comprises a carrier.

13. The skin care composition according to claim 1, wherein the composition comprises coffee seed oil extracted from roasted seeds of coffee from *Coffea arabica*.

14. The skin care composition according to claim 1, wherein the composition comprises water in an amount of 35 to 85% by weight of the composition.

15. The skin care composition according to claim 1, wherein the composition is of the wash-off type.

16. The skin care composition according to claim 12, wherein the carrier comprises a water-in-oil or oil-in-water emulsion.

17. The skin care composition according to claim 12, wherein the carrier comprises an oil-in-water emulsion.

18. The skin care composition according to claim 1, wherein the coffee seed oil is present in an amount of 0.0001 to 5% by weight of the composition.

19. A method for providing benefits selected from anti-inflammation, anti-aging, and anti-acne comprising the step of applying the skin care composition according to claim 1, to the skin of an individual in need thereof.

\* \* \* \* \*